United States Patent
Pawlak (10) Patent No.: US 11,633,628 B2
(45) Date of Patent: Apr. 25, 2023

(54) MONITOR FOR HIGH DOSE RATE ELECTRON THERAPY, SYSTEM AND METHOD

(71) Applicant: Varian Medical Systems, Inc., Palo Alto, CA (US)

(72) Inventor: Daniel Pawlak, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 17/353,538

(22) Filed: Jun. 21, 2021

(65) Prior Publication Data
US 2022/0401757 A1   Dec. 22, 2022

(51) Int. Cl.
*A61N 5/10* (2006.01)
*G01T 1/02* (2006.01)

(52) U.S. Cl.
CPC .............. *A61N 5/1071* (2013.01); *G01T 1/02* (2013.01); *A61N 2005/1089* (2013.01)

(58) Field of Classification Search
None
See application file for complete search history.

(56) References Cited

U.S. PATENT DOCUMENTS

| | | | | |
|---|---|---|---|---|
| 3,165,629 | A | * | 1/1965 | Okabe ...................... G01T 1/28 250/389 |
| 4,206,355 | A | | 6/1980 | Boux |
| 4,976,266 | A | * | 12/1990 | Huffman ................. G01T 1/161 250/371 |
| 5,326,976 | A | * | 7/1994 | Kikuchi .................. H01J 47/02 250/385.1 |
| 2017/0021198 | A1 | * | 1/2017 | Kawrykow .......... A61N 5/1077 |

FOREIGN PATENT DOCUMENTS

| | | |
|---|---|---|
| JP | S4826310 | 8/1973 |
| JP | 2517646 | 7/1996 |
| WO | 2019025933 | 2/2019 |

OTHER PUBLICATIONS

Simona, Giordanengo et al, "Dose Delivery Concept and Instrumentation," arxiv.org, Cornell University Library, 201 Olin Library Cornell University, Ithaca, NY 14853, Feb. 14, 2018 (Feb. 14, 2018), pp. 1-35.

* cited by examiner

*Primary Examiner* — Hoon K Song (57) ABSTRACT

A radiotherapy dose rate monitor system includes an electrode configured to be impinged by radiotherapy radiation, and a current measurement circuit configured to measure a current through the electrode. An emission of secondary electrons emitted from the electrode provides a majority of current through the electrode.

20 Claims, 6 Drawing Sheets

```
START
  ↓
510 COUPLE AN ELECTRODE OF A SCATTERING / MEASURING
ELECTRODE TO A CURRENT MEASURING CIRCUIT
  ↓
520 EXPOSE THE ELECTRODE TO RADIOTHERAPY RADIATION
  ↓
530 MEASURE A CURRENT THROUGH THE ELECTRODE DUE TO
SECONDARY ELECTRON EMISSION FROM THE ELECTRODE TO
INDICATE A DOSE RATE OF THE RADIOTHERAPY RADIATION
  ↓
540 CONTROL DOSE RATE BASED ON THE INDICATION OF DOSE RATE
  ↓
End
```

Fig. 5

MONITOR FOR HIGH DOSE RATE ELECTRON THERAPY, SYSTEM AND METHOD

FIELD OF INVENTION

Embodiments of the present invention relate to the field of medical devices. More specifically, embodiments of the present invention relate to systems and methods for monitoring high dose rate electron beam therapy.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

It is critical to accurately measure the dose of such radiation during treatment. For example, radiotherapy is typically very precisely planned based on numerous factors, including, for example, tumor type, tumor location, and stage, as well as the general health of the patient. In general, too much radiation may harm a patient, and too little radiation may not achieve a desired therapeutic effect.

Conventionally, an ionization chamber is utilized to measure radiation dosage and/or dose rate based on radiation-induced ionization in a gas. A sample gas is enclosed in an ionization chamber between two electrodes. The radiation "beam" is directed through the ionization chamber prior to impacting a patient, causing some of the sample gas to be ionized. The ionization typically creates a negatively charged electron and a positive ion. A voltage applied to the electrodes, for example 500 volts, collects the electrons on the positive electrode and collects positive ions on the negative electrode. A current collected by these electrodes is generally proportional to the radiation dose rate, and may be measured to create a dose monitor. As long as the radiation ionizes only a small fraction of the gas, the current will be linear with respect to dose rate.

FLASH radiotherapy is an emerging radiotherapy regime that appears to reduce radiation-induced toxicities while maintaining a tumor response similar to that of more conventional radiotherapy regimes. FLASH radiotherapy may be characterized as delivering a high radiation rate, e.g., greater than about 40 grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, FLASH radiotherapy may deliver a similar total dose at a rate of 40 Gy/s, requiring a fraction of a second of treatment time.

However, when radiation dose rates are very high, as is the case with FLASH radiotherapy, conventional dosage monitoring devices become less accurate than desired. Due to the high radiation intensity, a great many electron/ion pairs are created such that electrons and ions make up a significant fraction of the sample gas, and ions/electrons from different tracks encounter each other on their way to the collecting electrode(s). As a result, recombination between electrons and ions occurs at a high rate that varies with the dose rate, and the measured current no longer corresponds linearly to the radiation dose rate. Thus, conventional dosage monitoring devices are generally not accurate enough for use with FLASH radiotherapy.

SUMMARY OF THE INVENTION

Therefore, what is needed are systems and methods for monitoring high dose rate electron beam therapy. What is additionally needed are systems and methods for monitoring high dose rate electron beam therapy that accurately measure radiotherapy doses of FLASH radiotherapy. Further, there is a need for systems and methods for monitoring high dose rate electron beam therapy that accurately measure radiotherapy doses of both conventional radiotherapy and FLASH radiotherapy. There is a further need for systems and methods for monitoring high dose rate electron beam therapy that are compatible and complementary with existing systems and methods of administering radiotherapy.

In accordance with an embodiment of the present invention, a radiotherapy dose rate monitor system includes an electrode configured to be impinged by radiotherapy radiation, and a current measurement circuit configured to measure a current through the electrode. An emission of secondary electrons emitted from the electrode provides a majority of current through the electrode.

According to another embodiment, a radiotherapy dose rate monitor system includes an electrode configured to be impinged by radiotherapy radiation, a resistor coupled to the electrode and to ground, and a voltage measurement device configured to measure a voltage through the resistor corresponding to a radiotherapy dose rate. The dose rate monitor system is operable in a first mode or a second mode. The first mode corresponds to a dose rate characteristic of FLASH radiotherapy and the second mode corresponds to a dose rate of less than 40 Gy/s.

According to another embodiment, a radiotherapy dose rate monitor system includes a first electrode, a first resistor configured to couple the first electrode to ground, and a first voltage sensor configured to measure a first voltage across the first resistor. The first voltage is indicative of a first radiation dose passing through the first electrode. The radiotherapy dose rate monitor system is configured to measure radiotherapy dose rates of greater than or equal to 40 Gy/s to an accuracy of better than 98% during patient treatment.

BRIEF DESCRIPTION OF THE DRAWINGS

The accompanying drawings, which are incorporated in and form a part of this specification, illustrate embodiments of the invention and, together with the description, serve to explain the principles of the invention. Unless otherwise noted, the drawings may not be drawn to scale.

DETAILED DESCRIPTION

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Some portions of the detailed descriptions which follow (e.g., method 500) are presented in terms of procedures, steps, logic blocks, processing, and other symbolic representations of operations on data bits that may be performed on computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, data, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "applying" or "controlling" or "generating" or "testing" or "heating" or "bringing" or "capturing" or "storing" or "reading" or "analyzing" or "resolving" or "accepting" or "selecting" or "determining" or "displaying" or "presenting" or "computing" or "sending" or "receiving" or "reducing" or "detecting" or "setting" or "accessing" or "placing" or "forming" or "mounting" or "removing" or "ceasing" or "stopping" or "coating" or "processing" or "performing" or "adjusting" or "creating" or "executing" or "continuing" or "indexing" or "translating" or "calculating" or "measuring" or "gathering" or "running" or the like, refer to the action and processes of, or under the control of, a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The meaning of "non-transitory computer-readable medium" should be construed to exclude only those types of transitory computer-readable media which were found to fall outside the scope of patentable subject matter under 35 U.S.C. § 101 in *In re Nuijten*, 500 F.3d 1346, 1356-57 (Fed. Cir. 2007). The use of this term is to be understood to remove only propagating transitory signals per se from the claim scope and does not relinquish rights to all standard computer-readable media that are not only propagating transitory signals per se.

In the following disclosure, exemplary embodiments in accordance with the present invention are illustrated in terms of a linear accelerator and radiotherapy particles, e.g., electrons. However, it will be appreciated by those skilled in the art that the same or similar principles apply to other systems, including, for example, cyclotrons, and other types of ionizing radiation, including, for example, photons, e.g., X-rays, protons, and/or other particles. All such systems are well suited to, and are within the scope of embodiments in accordance with the present invention.

In the following descriptions, various elements and/or features of embodiments in accordance with the present invention are presented in isolation so as to better illustrate such features and as not to unnecessarily obscure aspects of the invention. It is to be appreciated, however, that such features, e.g., as disclosed with respect to a first drawing, may be combined with other features disclosed in other drawings in a variety of combinations. All such embodiments are anticipated and considered, and may represent embodiments in accordance with the present invention.

Monitor for High Dose Rate Electron Therapy, System and Method

Figure 1:
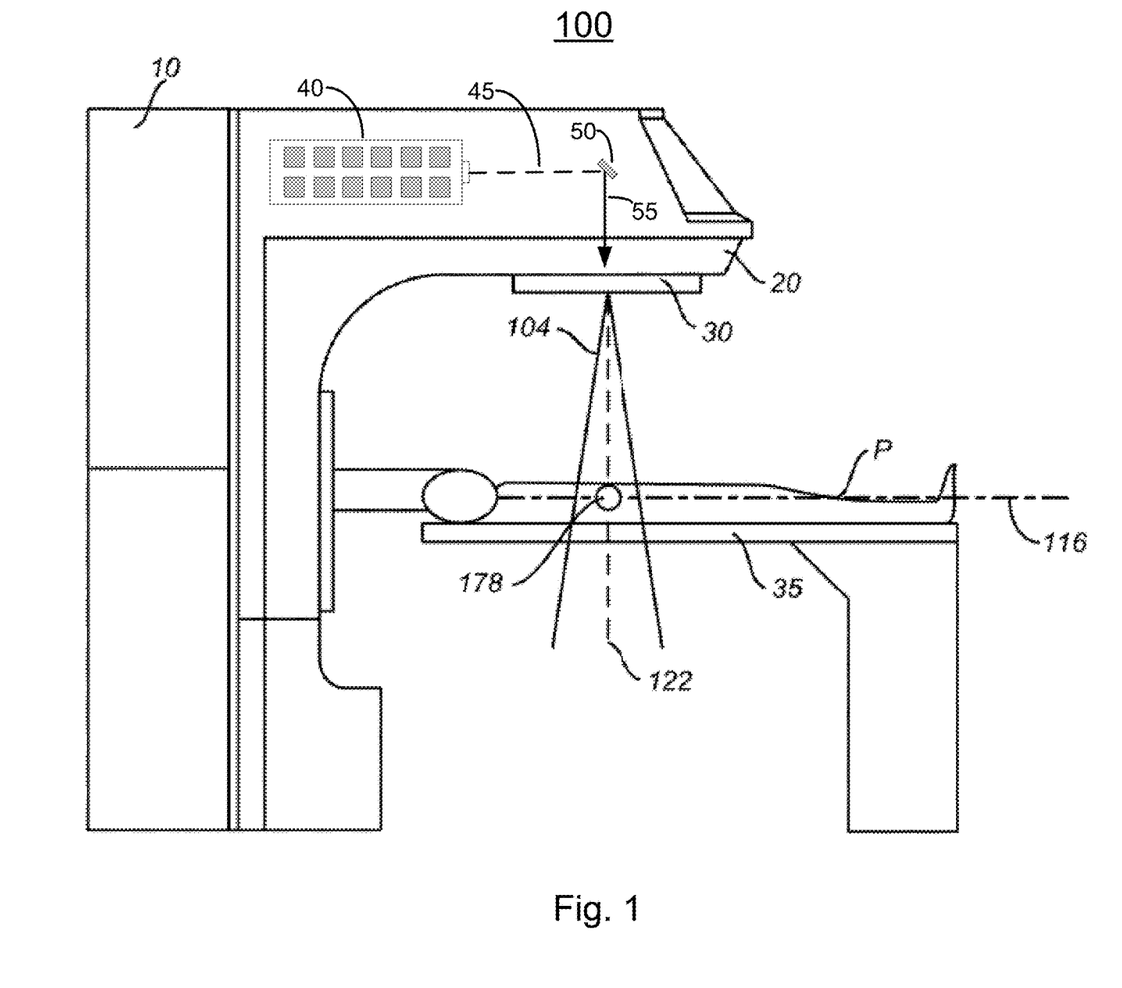
FIG. 1 illustrates a block diagram of an exemplary radiation treatment system that may serve as a platform for embodiments in accordance with the present invention.

FIG. 1 illustrates a block diagram of an exemplary radiation treatment system 100 that may serve as a platform for embodiments in accordance with the present invention. Radiation treatment system 100 may be similar to a True-Beam® radiotherapy system, commercially available from Varian Medical Systems, Palo Alto, Calif.

Stand 10 supports a rotatable gantry 20 with a treatment head 30. The treatment head 30 may extend into the gantry 20. In proximity to stand there is arranged a control unit (not shown) which includes control circuitry for controlling the different modes of operation of the system 100.

Radiation treatment system 100 comprises a linear accelerator 40, for example, within gantry 20, utilized to create a radiation beam. Typically, radiation treatment system 100 is capable of generating either an electron (particle) beam or an x-ray (photon) beam for use in the radiotherapy treatment of patients on a treatment couch 35. Other radiation treatment systems are capable of generating heavy ion particles such as protons. For purposes of the following disclosure, only electron irradiation will be discussed.

A high voltage source is provided within the stand and/or in the gantry to supply voltage to an electron gun (not shown) positioned on an accelerator guide located in the gantry 20. Electrons are emitted from the electron gun into the accelerator 40 where they are accelerated. A source supplies radio frequency (microwave) power for the generation of an electric field within the waveguide. The electrons emitted from the electron gun are accelerated in the waveguide by the electric field, and exit the waveguide as a high-energy electron beam 45, for example, at megavoltage energies. The electron beam 45 then strikes a suitable metal reflector 50, redirecting high energy electrons 55 in the direction of a patient P. In some embodiments, the electrons 55 may be redirected toward the patient by a system of one or more bend magnets.

As illustrated in FIG. 1, a patient P is shown lying on the treatment couch 35. High energy electrons as described above are emitted from the treatment head 30 in a divergent beam 104. Typically, a patient plane 116, is positioned, for example, about one meter from the electron source, and the rotational axis of the gantry 20 is located on the plane 116, such that the distance between the target and the isocenter 178 remains constant when the gantry 20 is rotated. It is appreciated that for electron FLASH therapy, the patient plane 116 may be less than one meter from the electron source. The isocenter 178 is at the intersection between the patient plane 116 and the central axis of beam 122. A treatment volume to be irradiated may be located about the isocenter 178. It is appreciated that some treatment plans may utilize a primary target that is off of the central beam axis, and such arrangements are within the scope of embodiments in accordance with the present invention.

Figure 2:
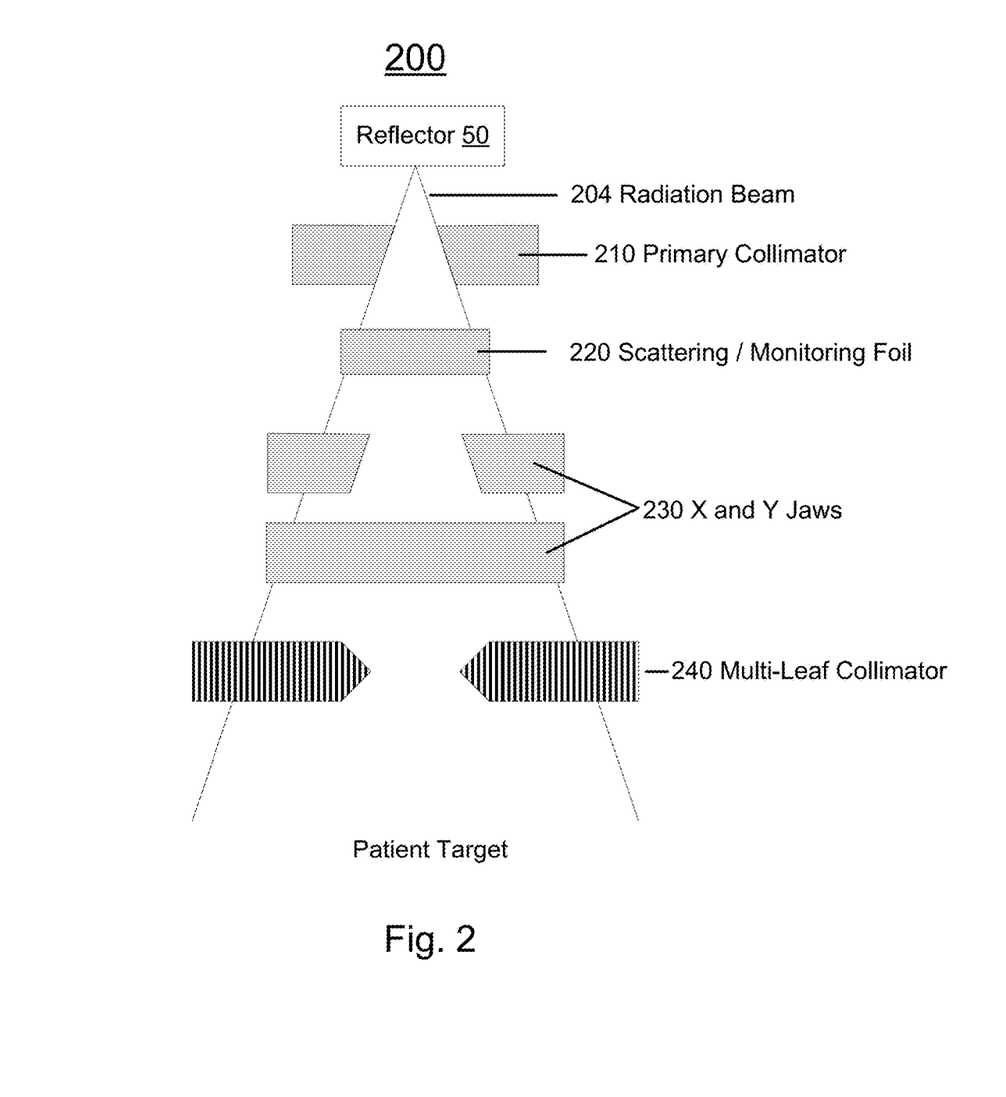
FIG. 2 illustrates a schematic of an exemplary beam path within an exemplary radiation treatment system, in accordance with embodiments of the present invention.

FIG. 2 illustrates a schematic of an exemplary beam path 200 within exemplary radiation treatment system 100, in accordance with embodiments of the present invention. It is appreciated that the illustrated components of beam path 200 are exemplary, and all may not be required in some embodiments. Additional components, e.g., a flattening filter (not shown), may also be included in accordance with embodiments of the present invention. A radiation beam 204 passes through primary collimator 210, X and Y jaws 230, and multi-leaf collimator 240. The primary collimator may comprise a plurality of selectable collimators and/or filters, in some embodiments. The primary collimator, X and Y jaws 230, and the leaves of the multi-leaf collimator (MLC) 240 typically comprise an electron blocking material, and are positioned in the head 30 (FIG. 1) to define the width of the electron beam at the patient plane. Typically, the X and Y jaws 230 are moveable and, when fully open, define a maximum beam width at the patient plane 116 (FIG. 1). The MLC 330 is positioned at the exit of the head 30, to further shape the electron beam. Exemplary MLCs may use up to 120 individually controllable leaves, for example, thin slices of tungsten, which may be moved into or out of the electron beam under the control of system software.

In accordance with embodiments of the present invention, a scattering/monitor foil 220 is placed within radiation beam 204. Generally, scattering/monitor foil 220 may be placed between a primary collimator 210 and X and Y jaws 230, although that is not required. Scattering/monitor foil may be utilized to spread, or "scatter," a radiotherapy beam, in some embodiments. For example, a very narrow or "tight" radiation beam is spread out to form a broader radiation field. Scattering/monitor foil 220 is further utilized to measure the radiation dose delivered by radiation beam 204, in accordance with embodiments of the present invention.

In some embodiments, a monitor foil may be separate from a scattering foil. For example, a radiotherapy system includes a conventional scattering foil and a separate, novel monitoring foil. Embodiments in accordance with the present invention are well suited to a separate monitor foil and/or a combined scattering/monitor foil.

Figure 3A:
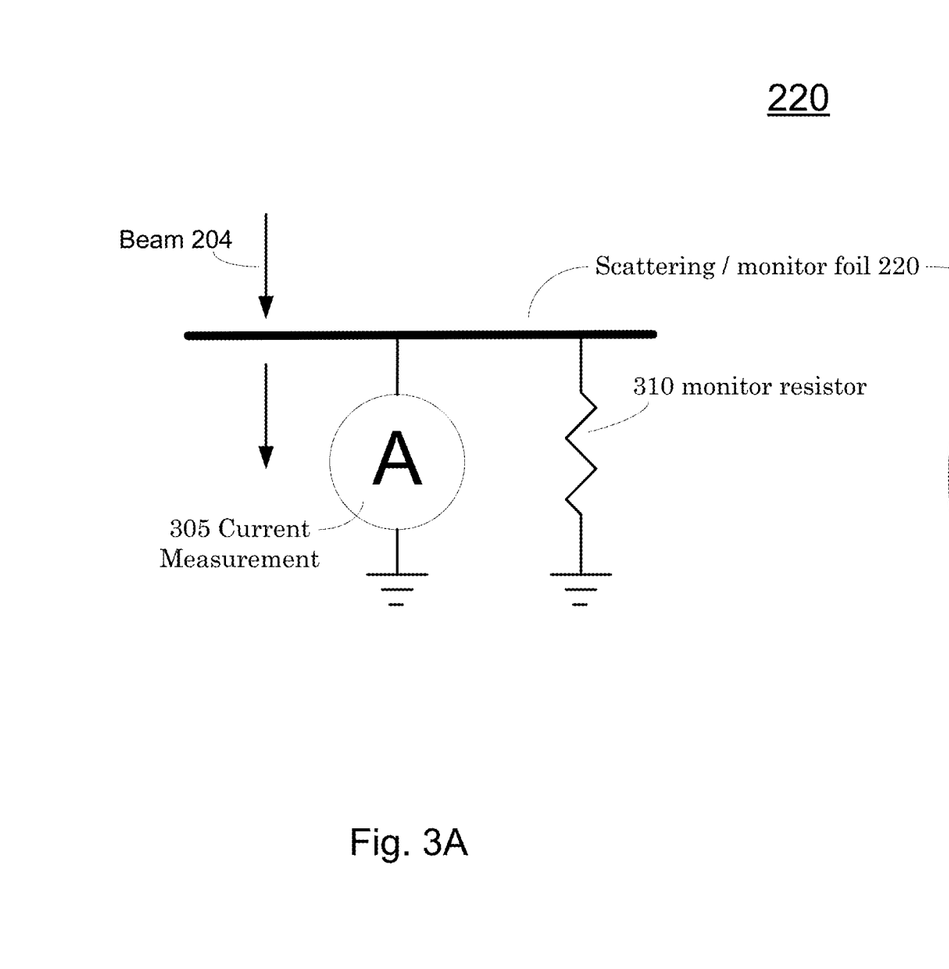
FIGS. 3A and 3B illustrate an exemplary scattering/monitoring foil, in accordance with embodiments of the present invention.
Figure 3B:
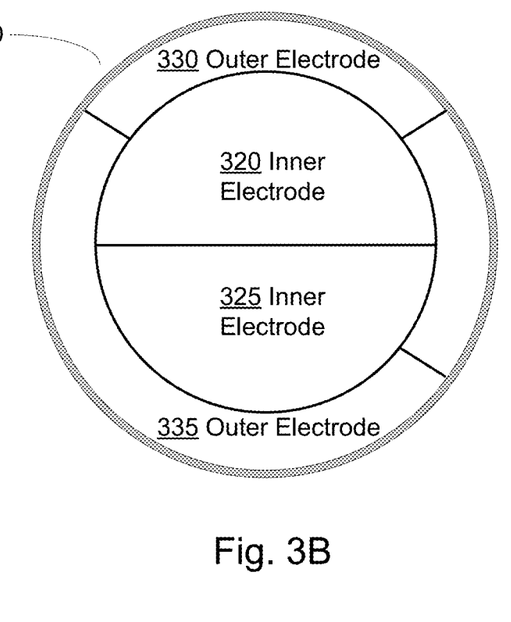

FIGS. 3A and 3B illustrate an exemplary scattering/monitor foil 220, in accordance with embodiments of the present invention. Scattering/monitor foil 220 may be utilized, for example, in radiation treatment system 100, to measure a radiation dose and/or dose rate, for example.

Scattering/monitor foil 220 typically provides closed loop feedback to portions of radiation treatment system 100 (FIG. 1) to control the intensity of beam 204. Scattering/monitor foil 220 typically also provides a record of a treatment dose. Scattering/monitor foil 220 may further function as part of an emergency shut off capability if a safe and/or a prescribed level of radiation is not achieved, e.g., too much or too little radiation. At least a portion of scattering/monitor foil 220 is positioned within radiation beam 204, as illustrated in FIG. 2. FIG. 3A illustrates a side-sectional view of an exemplary scattering/monitor foil 220, in accordance with embodiments of the present invention.

Scattering/monitor foil 220 may comprise a thin conductive foil, for example comprising aluminum 0.0007 inches (17.78 μm) thick. Other thicknesses, e.g., 0.0008 inches to 0.009 inches (20-230 μm), and materials, e.g., brass, copper, and/or gold, may be suitable. For example, thicker foils may be suited to higher electron energies. Conventionally, a scattering foil is electrically floating or grounded. In accordance with embodiments of the present invention, scattering/monitor foil 220 may be coupled to a current measuring circuit 305. As will be described further with respect to FIG. 4 below, current measuring circuit 305 is configured to measure a current due to the emission of secondary electrons from scattering/monitor foil 220 due to an impinging radiation beam, e.g., radiation beam 204. Any suitable current measuring circuit may be used, including, for example, electrical and/or magnetic circuits, and passive and/or active circuits.

In accordance with embodiments of the present invention, a resistor may be utilized to measure such a current. In some embodiments, scattering/monitor foil 220 is coupled to a relative ground, e.g., an earth ground, a chassis ground, a local ground, a current return path, and/or an electron source, via a monitoring resistor 310. An exemplary resistance value for monitoring resistor 310 is 50 ohms, in some embodiments. Other resistance values may be suitable. For example, different resistance values may be suited to different dosage rates. In some embodiments, the monitoring resistor 310 may be utilized to couple thermal energy away from the monitor foil. It is appreciated that monitor resistor 310 is an example of a current measurement circuit 305, and that generally only one type of current measurement circuit would be utilized per electrode.

Scattering/monitor foil 220 may comprise multiple electrodes in some embodiments. Such multiple electrodes may be mounted to a separate substrates and/or formed by an electrical interruption in a substantially planar and/or foil structure. FIG. 3B illustrates a plan view of an exemplary arrangement of a four-electrode scattering/monitor foil 220, in accordance with embodiments of the present invention. Embodiments in accordance with the present invention are well suited to more or fewer electrodes, as well as to different shape(s) and orientations of electrodes. In embodiments comprising multiple electrodes, each electrode should be electrically isolated from any other electrodes, and each electrode should be separately grounded via a separate instance of a monitoring resistor 310 (not shown in FIG. 3B). It is appreciated that all electrodes are not required to be the same shape, in some embodiments. It is further appreciated that all instances of a monitoring resistor 310 are not required to comprise the same resistance value and/or be of the same construction, in some embodiments. In some embodiments, monitoring resistor 310 is located outside of radiotherapy beam 204.

Exemplary scattering/monitoring foil 220 comprises four electrodes: inner electrode 320, inner electrode 325, outer electrode 330, and outer electrode 335. The inner electrodes, 320 and 325, may be configured to be completely within the incident radiation beam 204. The inner electrodes, 320 and 325, may be configured to measure a total dose rate of the incident radiation beam 204. Any dose rate difference between inner electrodes 320 and 325 may reveal a beam 204 angle symmetry error.

The outer electrodes, 330 and 335, may be configured to be partially within the beam 204, e.g., on an edge of beam 204. Any dose rate difference between outer electrodes 330 and 335 may reveal a beam 204 position symmetry error.

Figure 4:
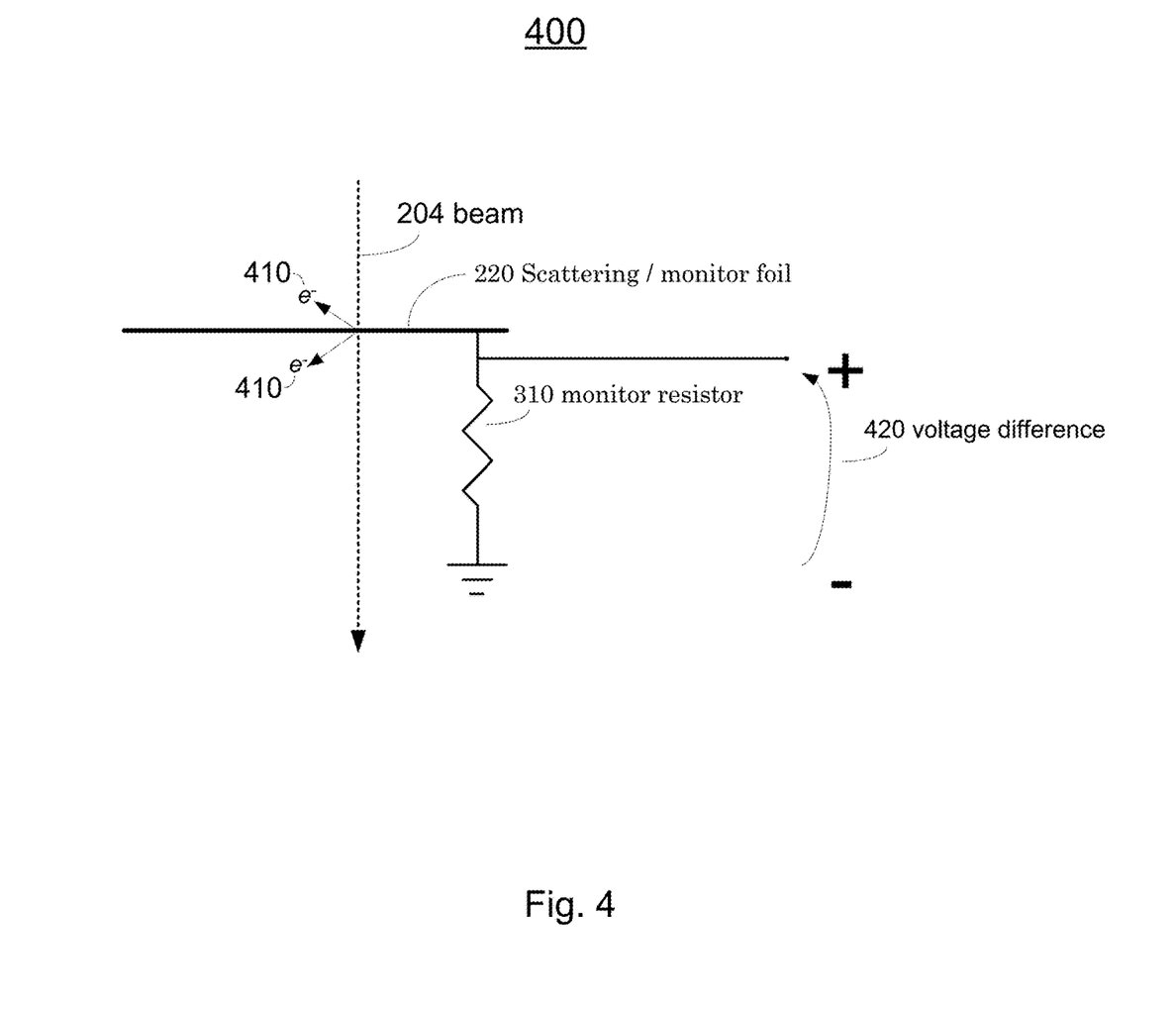
FIG. 4 illustrates a schematic diagram of an exemplary single electrode as part of a scattering/monitor foil, in accordance with embodiments of the present invention.

FIG. 4 illustrates a schematic diagram 400 of an exemplary single electrode as part of a scattering/monitor foil 220, in accordance with embodiments of the present invention. An electrode of scattering/monitor foil 220 is coupled to relative ground through current measuring circuit 305, embodied as monitor resistor 310 in a monitor resistor embodiment. Any additional electrodes (not shown) would be coupled to relative ground through current measuring circuits and/or parallel resistors. In some embodiments, during operation, radiation-therapy beam 204 passes through scattering/monitor foil 220, displacing secondary electrons 410. The secondary electrons 410 may render a positive charge on scattering/monitor foil 220, which may cause a current to flow through monitor resistor 310, resulting in a voltage difference 420 across monitor resistor 310. Electronic circuitry (not shown) may detect voltage difference 420, using voltage difference 420 as an indication of the dosage rate of radiotherapy beam 204.

In contrast to conventional radiotherapy dose rate monitors that may utilize a circuit comprising multiple electrodes, embodiments in accordance with the present invention utilize a circuit having a single electrode. In addition, embodiments in accordance with the present invention do not require a voltage externally applied to the electrode.

It is anticipated that some radiotherapy dosage regimes may cause a negative charge to accumulate on an electrode of a scattering/monitor foil 220. Such a circumstance would reverse the current and voltage difference described previously, and is considered within the scope of embodiments in accordance with the present invention.

Radiotherapy is typically delivered in very short pulses. For example, a conventional radiotherapy system may deliver 360 pulses per second, with each pulse having a duration of about 4 μs. Each pulse may provide a dose of about 1 mGy, for example. Such an exemplary protocol delivers about 0.4 Gy/s on a time average basis. FLASH radiotherapy may be characterized as delivering a radiation dose greater than or equal to 40 grays (Gy) per second, on a time average basis. Embodiments in accordance with the present invention enable accurate dosage and dosage-rate measurements of FLASH radiotherapy, thereby enabling therapeutic use of FLASH radiotherapy.

At high radiation intensities, e.g., equal to or greater than about 2 mGy per 4 us pulse, conventional dosage monitoring devices, e.g., ion chambers, are generally not accurate enough for use with high intensity and/or FLASH radiotherapy. For example, such conventional dosage monitoring devices are generally not able to achieve greater than or equal to 98% accuracy in reporting high intensity and/or FLASH radiotherapy dose rates. Embodiments in accordance with the present invention are able to provide greater than or equal to 98% accuracy in reporting high intensity and/or FLASH radiotherapy dose rates, e.g., greater than or equal to 40 Gy/s. Accuracy may be determined in comparison to other well-known dosimeter devices that are typically not used during treatment, including, for example, external probes and/or film dosimeters.

Referring once again to FIG. 1, many conventional radiotherapy systems are designed to rotate around the isocenter 178 of patient P, in order to distribute a radiation dose over all of the surrounding tissue while delivering an entire dose to the target tissue. One potential benefit of FLASH radiotherapy is that it appears to reduce radiation-induced damage to surrounding tissues while maintaining a tumor response equivalent to that of more conventional radiotherapy regimes. This benefit of FLASH radiotherapy may reduce the benefit(s) of such rotation. Embodiments in accordance with the present invention provide systems and methods of accurately measuring dose and/or dose rates of FLASH radiotherapy. Accordingly, embodiments in accordance with the present invention may facilitate non-rotational FLASH radiotherapy, beneficially reducing the cost, complexity, and room-size requirements of such radiotherapy systems.

Conventional radiotherapy dose rate measurement systems, e.g., based on ion chambers, may produce an electrical current based on ionization of a gas and/or emission of secondary electrons, e.g., from chamber electrodes. A portion of current from either source may vary based on the design of ion chamber and/or the radiotherapy intensity. In contrast, in accordance with embodiments of the present invention, a majority of current corresponding to a radiotherapy dose rate is produced by secondary electrons emitted from the electrode. Such a single current producing mechanism may be advantageous for calibration of dose rate measurements across a wide range of radiotherapy dosage rates.

As previously presented, when radiotherapy dose rates are very high, as is the case with FLASH radiotherapy, conventional dosage monitoring devices become less accurate than desired. Embodiments in accordance with the present invention enable accurate dosage monitoring for high radiation dose rates. In addition, embodiments in accordance with the present invention are capable of providing accurate dosage monitoring for lower and/or conventional radiation dose rates, e.g., dose rates at less that FLASH radiotherapy rates. Accordingly, embodiments in accordance with the present invention may be operated in at least two modes, for example, a first mode that corresponds to a dose rate characteristic of FLASH radiotherapy, and a second mode that corresponds to a dose rate of less than 40 Gy/s. In some embodiments, calibration of current measurement(s) may vary among such mode(s), although that is not required.

Figure 5:
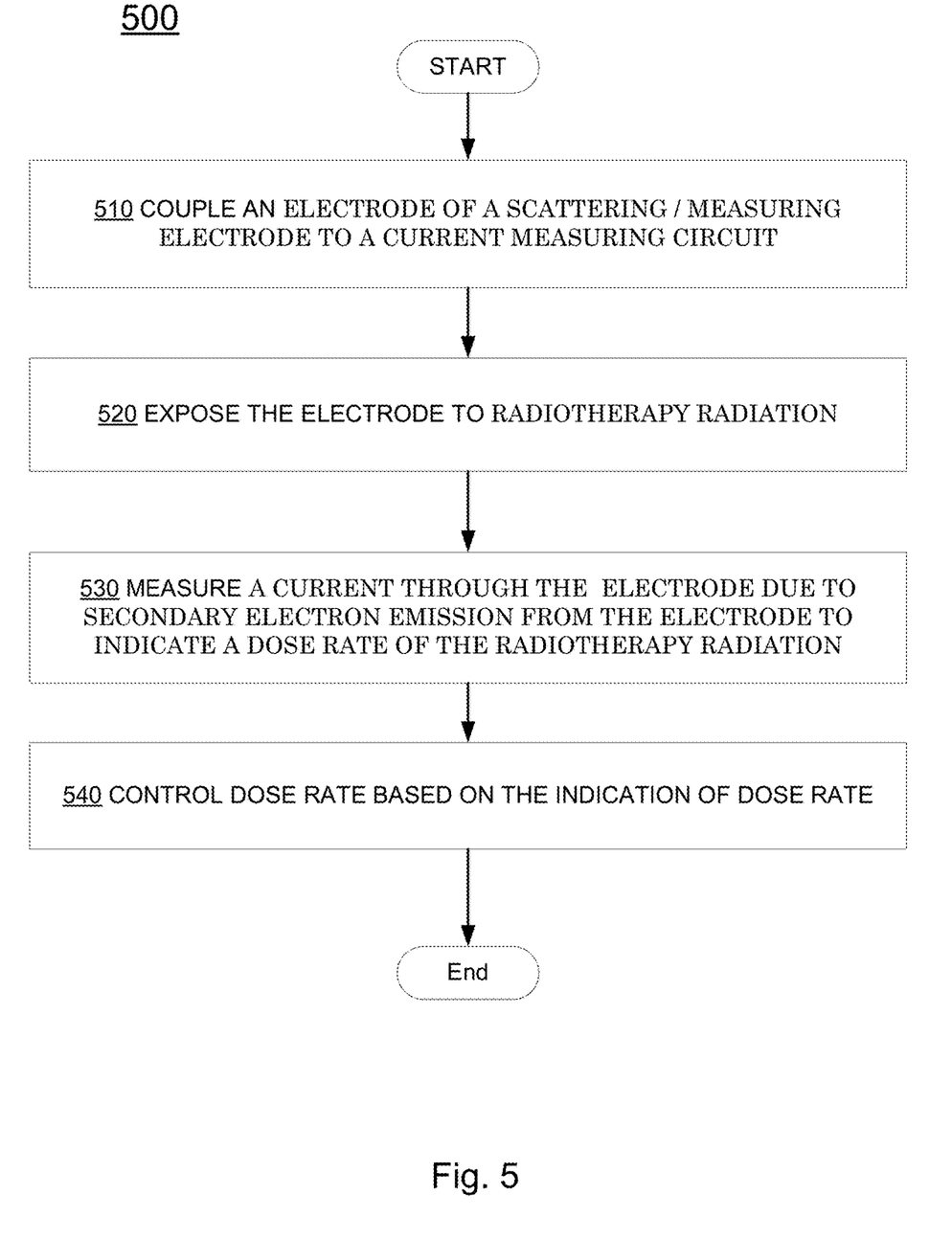
FIG. 5 is a simplified flowchart of an exemplary method of measuring a radiotherapy dose rate, in accordance with embodiments of the present invention.

FIG. 5 is a simplified flowchart of an exemplary method 500 of measuring a radiotherapy dose rate, in accordance with embodiments of the present invention. Method 500 may be performed wholly or partially with a computer system, e.g., computer system 600 of FIG. 6.

In 510, an electrode, e.g., of a scattering/measuring foil 220 (FIG. 4), is coupled to a current measuring circuit, e.g., current measuring circuit (FIG. 3A). The current measuring circuit may comprise coupling the scattering/measuring foil 220 to a relative ground via a resistor, e.g., monitor resistor 310 (FIG. 3A). In 520, the electrode is exposed to radiotherapy radiation. The radiotherapy radiation may be at dose rate intensities corresponding to FLASH radiotherapy.

In 530, a current through the electrode is measured. For example, a voltage across the resistor due to secondary electron emission from the electrode is measured to indicate a dose rate of the radiotherapy radiation. In optional 540, the indication of dose rate is used as feedback to control a dose rate of FLASH radiotherapy.

Figure 6:
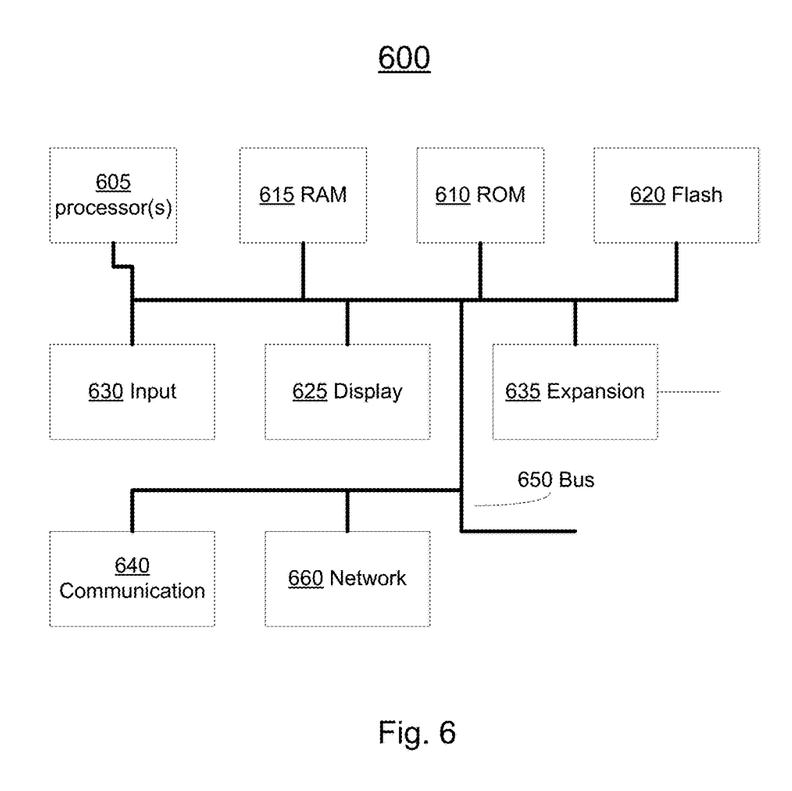
FIG. 6 illustrates a block diagram of an exemplary electronic system, which may be used as a platform to implement and/or as a control system for embodiments of the present invention.

FIG. 6 illustrates a block diagram of an exemplary electronic system 600, which may be used as a platform to implement and/or as a control system for embodiments of the present invention. Electronic system may be a "server" computer system, in some embodiments. Electronic system 600 includes an address/data bus 650 for communicating information, a central processor complex 605 functionally coupled with the bus for processing information and instructions. Bus 650 may comprise, for example, a Peripheral Component Interconnect Express (PCIe) computer expansion bus, industry standard architecture (ISA), extended ISA (EISA), MicroChannel, Multibus, IEEE 796, IEEE 1196, IEEE 1496, PCI, Computer Automated Measurement and Control (CAMAC), MBus, Runway bus, Compute Express Link (CXL), and the like.

Central processor complex 605 may comprise a single processor or multiple processors, e.g., a multi-core processor, or multiple separate processors, in some embodiments. Central processor complex 605 may comprise various types of well-known processors in any combination, including, for example, digital signal processors (DSP), graphics processors (GPU), complex instruction set (CISC) processors, reduced instruction set (RISC) processors, and/or very long word instruction set (VLIW) processors. In some embodiments, exemplary central processor complex 605 may comprise a finite state machine, for example, realized in one or more field programmable gate array(s) (FPGA), which may operate in conjunction with and/or replace other types of processors to control embodiments in accordance with the present invention.

Electronic system 600 may also include a volatile memory 615 (e.g., random access memory RAM) coupled with the bus 650 for storing information and instructions for the central processor complex 605, and a non-volatile memory 610 (e.g., read only memory ROM) coupled with the bus for storing static information and instructions for the processor complex 605. Electronic system 600 also optionally includes a changeable, non-volatile memory 620 (e.g., NOR flash) for storing information and instructions for the central processor complex 605 which can be updated after the manufacture of system 600. In some embodiments, only one of ROM 610 or Flash 620 may be present.

Also included in electronic system 600 of FIG. 6 is an optional input device 630. Device 630 can communicate information and command selections to the central processor 600. Input device 630 may be any suitable device for communicating information and/or commands to the electronic system 600. For example, input device 630 may take the form of a keyboard, buttons, a joystick, a track ball, an audio transducer, e.g., a microphone, a touch sensitive digitizer panel, eyeball scanner, and/or the like.

Electronic system 600 may comprise a display unit 625. Display unit may comprise a liquid crystal display (LCD) device, cathode ray tube (CRT), field emission device (FED, also called flat panel CRT), light emitting diode (LED), plasma display device, electro-luminescent display, electronic paper, electronic ink (e-ink) or other display device suitable for creating graphic images and/or alphanumeric characters recognizable to the user. Display unit 625 may have an associated lighting device, in some embodiments.

Electronic system 600 also optionally includes an expansion interface coupled with the bus 650. Expansion interface 635 can implement many well known standard expansion interfaces, including without limitation the Secure Digital Card interface, universal serial bus (USB) interface, Compact Flash, Personal Computer (PC) Card interface, CardBus, Peripheral Component Interconnect (PCI) interface, Peripheral Component Interconnect Express (PCI Express), mini-PCI interface, IEEE 1394, Small Computer System Interface (SCSI), Personal Computer Memory Card International Association (PCMCIA) interface, Industry Standard Architecture (ISA) interface, RS-232 interface, and/or the like. In some embodiments of the present invention, expansion interface 635 may comprise signals substantially compliant with the signals of bus 650.

A wide variety of well-known devices may be attached to electronic system 600 via the bus 650 and/or expansion interface 635. Examples of such devices include without limitation rotating magnetic memory devices, flash memory devices, digital cameras, wireless communication modules, digital audio players, and Global Positioning System (GPS) devices.

System 600 also optionally includes a communication port 640. Communication port 640 may be implemented as part of expansion interface 635. When implemented as a separate interface, communication port 640 may typically be used to exchange information with other devices via communication-oriented data transfer protocols. Examples of communication ports include without limitation RS-232 ports, universal asynchronous receiver transmitters (UARTs), USB ports, infrared light transceivers, ethernet ports, IEEE 1394, and synchronous ports.

System 600 optionally includes a network interface 660, which may implement a wired or wireless network interface. Electronic system 600 may comprise additional software and/or hardware features (not shown) in some embodiments.

Various modules of system 600 may access computer readable media, and the term is known or understood to include removable media, for example, Secure Digital ("SD") cards, CD and/or DVD ROMs, diskettes and the like, as well as non-removable or internal media, for example, hard drives, solid state drive s (SSD), RAM, ROM, flash, and the like.

Embodiments in accordance with the present invention provide systems and methods for monitoring high dose rate electron beam therapy. In addition, embodiments in accordance with the present invention provide systems and methods for monitoring high dose rate electron beam therapy that accurately measure radiotherapy doses of FLASH radiotherapy. Further, embodiments in accordance with the present invention provide systems and methods for monitoring high dose rate electron beam therapy that accurately measure radiotherapy doses of both conventional radiotherapy and FLASH radiotherapy. Further, embodiments in accordance with the present invention provide systems and methods for monitoring high dose rate electron beam therapy that are compatible and complementary with existing systems and methods of administering radiotherapy.

Although the invention has been shown and described with respect to a certain exemplary embodiment or embodiments, equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

Various embodiments of the invention are thus described. While the present invention has been described in particular embodiments, it should be appreciated that the invention should not be construed as limited by such embodiments, but rather construed according to the below claims.

I claim:

1. A radiotherapy dose rate monitor system comprising:
   an electrode configured to be impinged by radiotherapy radiation;
   a current measurement circuit configured to measure a current through said electrode, and
   wherein emission of secondary electrons emitted from said electrode provides a majority of current through said electrode.

2. The radiotherapy dose rate monitor system of claim 1, wherein said current measurement circuit comprises a resistor.

3. The radiotherapy dose rate monitor system of claim 2, wherein said resistor is located outside of a beam of said radiotherapy radiation.

4. The radiotherapy dose rate monitor system of claim 2, wherein said resistor is configured to remove heat from said electrode.

5. The radiotherapy dose rate monitor system of claim 1, wherein said electrode comprises a foil.

6. The radiotherapy dose rate monitor system of claim 5, wherein said foil comprises aluminum.

7. The radiotherapy dose rate monitor system of claim 1, further comprising:
   a scattering foil separate from said electrode.

8. A radiotherapy dose rate monitor system comprising:
   an electrode configured to be impinged by radiotherapy radiation;
   a resistor coupled to said electrode and to relative ground;
   a voltage measurement device configured to measure a voltage through said resistor corresponding to a radiotherapy dose rate,
   wherein said dose rate monitor system is operable in a first mode or a second mode,
   wherein said first mode corresponds to a dose rate characteristic of FLASH radiotherapy, and
   wherein said second mode corresponds to a dose rate of less than 40 Gy/s.

9. The radiotherapy dose rate monitor system of claim 8, wherein said electrode comprises a foil.

10. The radiotherapy dose rate monitor system of claim 9, wherein said foil is less than 0.001 inches thick.

11. The radiotherapy dose rate monitor system of claim 9, wherein said foil comprises brass.

12. The radiotherapy dose rate monitor system of claim 8, wherein said resistor is not impinged by said radiotherapy radiation.

13. The radiotherapy dose rate monitor system of claim 8, wherein said resistor is configured to remove heat from said electrode.

14. The radiotherapy dose rate monitor system of claim 8, further comprising:
    a scattering foil separate from said electrode.

15. A radiotherapy dose rate monitor system comprising:
    a first electrode;
    a first resistor configured to couple said first electrode to relative ground;
    a first voltage sensor configured to measure a first voltage across said first resistor,
    wherein said first voltage is indicative of a first radiation dose passing through said first electrode, and
    wherein said radiotherapy dose rate monitor system is configured to measure radiotherapy dose rates of greater than or equal to 40 Gy/s to an accuracy of better than 98% during patient treatment.

16. The radiotherapy dose rate monitor system of claim 15 further comprising:
    a second electrode in a plane of said first electrode;
    a second resistor configured to couple said second electrode to ground;
    a second voltage sensor configured to measure a second voltage across said second resistor,
    wherein said second voltage is indicative of a second radiation dose passing through second first electrode, and
    wherein a difference between said first and second voltages indicates a symmetry error of a radiotherapy beam.

17. The radiotherapy dose rate monitor system of claim 16, wherein said electrode comprises a foil.

18. The radiotherapy dose rate monitor system of claim 15, wherein a radiotherapy beam is configured to pass through a collimator prior to impinging said first electrode.

19. The radiotherapy dose rate monitor system of claim 15, wherein said first radiation does comprises electrons.

20. The radiotherapy dose rate monitor system of claim 15, wherein said first electrode is configured to scatter a radiotherapy beam.

* * * * *